United States Patent
Lamish et al.

(10) Patent No.: US 9,546,392 B2
(45) Date of Patent: Jan. 17, 2017

(54) MAGNETIC SEPARATION OF RARE CELLS

(71) Applicant: BIOCEP LTD., Safed (IL)

(72) Inventors: Aharon Lamish, Ramat Gan (IL); Ofer Klein, Upper Galilee (IL)

(73) Assignee: BIOCEP LTD., Yoqneam Ilit (IL)

( * ) Notice: Subject to any disclaimer, the term of this patent is extended or adjusted under 35 U.S.C. 154(b) by 0 days.

(21) Appl. No.: 14/976,895

(22) Filed: Dec. 21, 2015

(65) Prior Publication Data

US 2016/0108454 A1    Apr. 21, 2016

Related U.S. Application Data

(63) Continuation of application No. 13/574,557, filed as application No. PCT/IL2011/000068 on Jan. 20, 2011, now Pat. No. 9,217,131.

(60) Provisional application No. 61/296,905, filed on Jan. 21, 2010.

(51) Int. Cl.
| | |
|---|---|
| *G01N 30/00* | (2006.01) |
| *B01J 19/08* | (2006.01) |
| *G01N 31/00* | (2006.01) |
| *C12Q 1/24* | (2006.01) |
| *B03C 1/033* | (2006.01) |
| *B03C 1/28* | (2006.01) |

(Continued)

(52) U.S. Cl.
CPC ............... *C12Q 1/24* (2013.01); *B03C 1/0335* (2013.01); *B03C 1/288* (2013.01); *C12M 47/02* (2013.01); *C12N 1/02* (2013.01); *B03C 2201/26* (2013.01)

(58) Field of Classification Search
USPC .......................... 422/73, 186.01; 436/10, 526
See application file for complete search history.

(56) References Cited

U.S. PATENT DOCUMENTS

| | | |
|---|---|---|
| 4,710,472 A | 12/1987 | Saur |
| 5,432,054 A | 7/1995 | Saunders |
| 5,457,024 A | 10/1995 | Goldbard |

(Continued)

FOREIGN PATENT DOCUMENTS

| | | |
|---|---|---|
| CN | 101305087 | 11/2008 |
| JP | 06505673 | 6/1994 |

(Continued)

OTHER PUBLICATIONS

Anderson et al. "Understanding drug release frompoly(ethylene oxide)-b-poly(propylene oxide)-b-poly (ethylene oxide) gels", J Controlled Rel, 70(1-2)151-167 (2001).

(Continued)

*Primary Examiner* — Dean Kwak
(74) *Attorney, Agent, or Firm* — The Roy Gross Law Firm, LLC; Roy Gross

(57) ABSTRACT

A magnetic separation system configured to separate with high qualitative and quantitative yield magnetized cells from cell mixtures, comprising at least one electromagnet structured to generate a magnetic field flux about a plurality of separation zones and sufficient to attract a majority of the magnetized cells in the mixture, and a pump to drive the cell mixture at a controlled flow rate through a tube disposed within the zones thereby separating a majority of the magnetized cells from the mixture. The system is particularly useful to retrieve rare cells from a fluid mixture of cells having low abundance of the rare cells relative to the rest of the cells while sustaining viability of the cells.

10 Claims, 5 Drawing Sheets

(51) Int. Cl.
*C12M 1/00* (2006.01)
*C12N 1/02* (2006.01)

(56) References Cited

U.S. PATENT DOCUMENTS

| | | | |
|---|---|---|---|
| 5,489,386 A | 2/1996 | Saunders | |
| 5,541,072 A | 7/1996 | Wang | |
| 5,629,147 A | 5/1997 | Asgari | |
| 5,641,628 A | 6/1997 | Bianchi | |
| 5,646,004 A | 7/1997 | Van Vlasselaer | |
| 5,656,001 A | 8/1997 | Baatz | |
| 5,731,156 A | 3/1998 | Golbus | |
| 5,750,339 A | 5/1998 | Smith | |
| 5,759,793 A | 6/1998 | Schwartz | |
| 5,764,792 A | 6/1998 | Kennealy | |
| 5,766,843 A | 6/1998 | Asgari | |
| 5,795,470 A | 8/1998 | Wang | |
| 5,858,649 A | 1/1999 | Asgari | |
| 5,861,253 A | 1/1999 | Asgari | |
| 5,962,234 A | 10/1999 | Golbus | |
| 5,993,632 A | 11/1999 | Becker | |
| 6,013,188 A | 1/2000 | Terstappen | |
| 6,143,577 A | 11/2000 | Bisconte De Saint Julien | |
| 6,169,816 B1 | 1/2001 | Ravkin | |
| 6,259,807 B1 | 7/2001 | Ravkin | |
| 6,331,395 B1 | 12/2001 | Burchell | |
| 6,432,630 B1 | 8/2002 | Blankenstein | |
| 6,482,328 B1 | 11/2002 | Davidson | |
| 7,166,443 B2 | 1/2007 | Walker | |
| 7,364,921 B1 | 4/2008 | Sciorra | |
| 7,749,445 B2 * | 7/2010 | Masters | B01L 3/502761 422/534 |
| 2002/0006621 A1 | 1/2002 | Bianchi | |
| 2002/0081014 A1 | 6/2002 | Ravkin | |
| 2002/0127616 A1 | 9/2002 | Burchell | |
| 2002/0137088 A1 | 9/2002 | Bianchi | |
| 2002/0182654 A1 | 12/2002 | Jing | |
| 2003/0044832 A1 | 3/2003 | Blankenstein | |
| 2003/0062314 A1 * | 4/2003 | Davidson | B03C 1/005 210/695 |
| 2003/0092078 A1 | 5/2003 | Thomas | |
| 2003/0134416 A1 | 7/2003 | Yamanishi | |
| 2003/0159976 A1 | 8/2003 | Iwasaki | |
| 2003/0185817 A1 | 10/2003 | Thomas | |
| 2004/0018509 A1 | 1/2004 | Bianchi | |
| 2004/0091880 A1 | 5/2004 | Wiebusch | |
| 2004/0142463 A1 | 7/2004 | Walker | |
| 2005/0124009 A1 | 6/2005 | Van Weeghel | |
| 2005/0287547 A1 | 12/2005 | Seligman | |
| 2006/0051775 A1 | 3/2006 | Bianchi | |
| 2006/0105353 A1 | 5/2006 | Jalal | |
| 2006/0223178 A1 | 10/2006 | Barber | |
| 2006/0252054 A1 | 11/2006 | Lin | |
| 2007/0015171 A1 | 1/2007 | Bianchi | |
| 2007/0026381 A1 | 2/2007 | Huang | |
| 2007/0059680 A1 | 3/2007 | Kapur | |
| 2007/0059683 A1 | 3/2007 | Barber | |
| 2007/0059716 A1 | 3/2007 | Balis | |
| 2007/0059718 A1 | 3/2007 | Toner | |
| 2007/0059719 A1 | 3/2007 | Grisham | |
| 2007/0059774 A1 | 3/2007 | Grisham | |
| 2007/0059781 A1 | 3/2007 | Kapur | |
| 2007/0172903 A1 | 7/2007 | Toner | |
| 2007/0196820 A1 | 8/2007 | Kapur | |
| 2007/0202536 A1 | 8/2007 | Yamanishi | |
| 2007/0207548 A1 | 9/2007 | Blankenstein | |
| 2007/0259424 A1 | 11/2007 | Toner | |
| 2008/0026390 A1 | 1/2008 | Stoughton | |
| 2008/0050739 A1 | 2/2008 | Stoughton | |
| 2008/0070792 A1 | 3/2008 | Stoughton | |
| 2008/0090239 A1 | 4/2008 | Shoemaker | |
| 2008/0113358 A1 | 5/2008 | Kapur | |
| 2008/0124721 A1 | 5/2008 | Fuchs | |
| 2008/0138809 A1 | 6/2008 | Kapur | |
| 2008/0182261 A1 | 7/2008 | Bianci | |
| 2008/0206757 A1 | 8/2008 | Lin | |
| 2008/0248499 A1 | 10/2008 | Chiu | |
| 2008/0254460 A1 | 10/2008 | Levicar | |
| 2009/0011409 A1 | 1/2009 | Sharma | |
| 2009/0081689 A1 | 3/2009 | Yamanishi | |
| 2009/0181421 A1 | 7/2009 | Kapur | |
| 2009/0220933 A1 | 9/2009 | Kolvraa | |
| 2009/0220955 A1 | 9/2009 | Verrant | |
| 2009/0280492 A1 | 11/2009 | Stoughton | |
| 2009/0291443 A1 | 11/2009 | Stoughton | |
| 2009/0305236 A1 | 12/2009 | Boehmer | |
| 2012/0046203 A1 * | 2/2012 | Walsh | A61B 5/157 506/39 |
| 2012/0149021 A1 * | 6/2012 | Yung | B03C 1/01 435/6.12 |

FOREIGN PATENT DOCUMENTS

| | | |
|---|---|---|
| JP | 2002515319 | 5/2002 |
| JP | 2006516890 | 7/2006 |
| WO | 2007/035498 | 3/2007 |

OTHER PUBLICATIONS

Bianchi, Diana W. et al., Isolation of fetal DNA from nucleated erythrocytes in maternal blood, Proc Natl Acad Sci USA, 87(9): 3279-3283 (1990).

Bianchi, Diana W. et al., Male fetal progenitor cells persist in maternal blood for as long as 27 years postpartum, Proc Natl Acad Sci USA, 93(2): 705-708 (1996).

Bianchi, Diana W. et al., PCR quantitation of fetal cells in maternal blood in normal and aneuplod pregnancies, Am J HUm Genet, 61(4): 822-829 (1997).

Bianchi, Diana W. et al., Fetal gender aneuploidy detection using fetal cells in maternal blood: analysis of NIFTY I data, National Institute of Child Health and Development Fetal Cell Isolation Study, Prenat Diagn, 22(7): 609-615 (2002).

Chiu, Rossa W. et al., Noninvasive prenatal diagnosis of fetal chromosomal aneuploidy by massively parallel genomic sequencing of DNA in maternal plasma, Proc Natl Acad Sci USA, 105(51):20458-20463 (2008).

Desai, Suketo et al., "Pluronic F127-Based Ocular Delivery System Containing Biodegradable Polyisobutylcyanoacrylate Nnaocapsules of Pilocarpine", Drug Del, 7(4)201-207 (2002).

El Banna et al., "Physicochemical and dissolution studies of phenylbutazone binary systems" Pharma Acta Helv, 55(10): 256-260 (1980).

El-Kamel, A.H. "In vitro and in vivo evaluation of Pluronic F127-based ocular delivery system for timolol maleate", Int J Pharm, 241(1):47-55 (2002).

Holland, Richard et al., "Fluorescence Probe Studies of Ethylene Oxide/Propylene Oxide Block Copolymers in Aqueous Solution", J Phys Chem, 99(31): 11981-11988 (1995).

Lamvu, Georgine et al. "Prenatal diagnosis using fetal cells from the maternal circulation" Obstet Gynecol Survey, 52(7):433-437 (1997).

Lin, Shan-Yang et al., "Pluronic surfactants affecting diazepam solubility, compatability and adsorption from i.v. admixture solutions", J Parent Sci Technol, 41(3):83-87 (1987).

Passerini, Nadia et al., "Preparation and characterization of ibuprofen-poloxamer 188 granules obtained by melt granulation", Eur J Pharm Sci, 15(1):71-78 (2002).

Quadir, M. et al., Evaluation of Lutrol F Grades (Prill vs Micronized) as a potential drug delivery system. BASF Corporation, available at www.aapsj.org/abstracts/AM_2002/AAPS2002-000134.pdf (2002).

Vandervoort et al., "Biocompatible stabilizers in the preparation of PLGA nanoparticles: a factorial design study", Int J Pharm, 238(1-2)77-92 (2002).

Vippagunta et al., "Solid-state characterization of nifedipine solid/dispersions", Int J Pharm, 236(1-2):111-123 (2002).

(56) References Cited

OTHER PUBLICATIONS

Walknowska et al., "Practical and theoretical implications of fetal/maternal lymphocyte transfer", Lancet, 293(7606): 1119-1122 (1969).

Wessman et al., "Fetal granulocytes in maternal venous blood detected by in situ hybridization", Prenat Diagn, 12(12): 993-1000 (1992).

* cited by examiner

MAGNETIC SEPARATION OF RARE CELLS

FIELD OF THE INVENTION

The invention relates to separation of particles including cells. Some embodiments of the invention relate to magnetic separation of rare cells.

BACKGROUND OF THE INVENTION

A large number of applications involving the magnetic separation of biological cells are described in the literature, for example in U.S. Pat. No. 4,710,472 and the many publications cited therein. Many such applications require not only the separation of one or more specific types of cells (hereinafter called "target cells"), but also the maintenance of the quality of the cell membranes in the target cells and/or in the untargeted cells. Thus, in a positive selection process, the target cells are separated from a sample for examination or use for research, diagnostic or clinical purposes; whereas in a depletion process, the sample is depleted of the target cells for examination or use of the untargeted cells. The separation of target cells from the untargeted cells, and the maintenance of the membranes of both the target cells and untargeted cells, are particularly important in research presently being conducted with lymphocyte populations and their role in the early detection of cancer.

One technique in present use for the separation of biological cells utilizes the MiniMACS Separation Columns (Miltenyi Biotec GmbH). This technique uses paramagnetic microbeads which are extremely small, about 50 nm in diameter, i.e., about one million times smaller in volume than that of eukaryotic cells, compared to the size of a virus. Such magnetic microbeads are produced with selective affinities for certain cells, i.e., the target cells, such that they magnetically label or stain the target cells. The sample is introduced into a magnetic separation column including a liquid-pervious magnetic body, e.g., steel wool or mesh, and a magnetic field is applied across the column such that the magnetically stained cells are retained in the liquid-pervious magnetic body of the column, while the unstained cells pass through the column. In this known process, however, it was found that the membranes of the cells are excessively damaged by the liquid-pervious magnetic body, which reduces the effectiveness of the technique for research or clinical purposes.

In some cases the target cells are rare in a sample, such as cancer cell, stem cells or fetal cells posing a challenge for the separation process. As a non-limiting example fetal cells are referred below.

The presence of fetal cells in maternal blood has been known for over a century since Schmorl (1) demonstrated trophoblast cells in the pulmonary circulation of women who died of eclampsia. Since then, five different fetal cell types have been demonstrated to circulate in maternal blood, including trophoblast cells (1), lymphocytes (2), nucleated erythrocytes (NRBCs) (3), granulocytes (4), and stem cells (5). The frequency of fetal cells in maternal circulation is very low, with an average of 1.2 cells/ml maternal blood as detected by a quantitative PCR technique (6). Among all of the fetal cell types isolated from maternal blood, NRBCs have emerged as the best candidate cells to be used in noninvasive prenatal diagnosis (7).

Researchers have attempted separation and enrichment of fetal NRBC using fluorescence activated cell sorting (FACS) and magnetic cell sorting (MACS) methods, including a large scale study funded by the NIH (NIFTY study). This study achieved low sensitivity of fetal cell detection with 13% recovery for FACS and 44% for MACS (the leading magnetic separation technology) (8) and concluded that as the proportion of fetal NRBC in maternal blood is low, and current separation techniques have low recovery rates, the utilization of FNRBC is not feasible for clinical application. As it is extremely difficult to separate these cells, alternative and less effective methods based on different genetic materials are explored, such as DNA fragments (9). These materials must be multiplied using PCR in order to effectively analyze them and cannot provide the same level of conclusive results regarding trisomies as FNRBCs might.

U.S. Pat. No. 6,482,328 to some of the inventors of the present invention and others discloses a method and apparatus for magnetically separating target particles of a selected type from a sample in order to produce concentration of the target particles in the sample, or depletion of the sample with respect to the target particles, by producing a sample mixture of the sample with magnetic particles having a selective affinity to magnetically stain the target particles.

There remains an unmet need for rapid and reliable magnetic separation of living rare cells with high yield and high purity.

SUMMARY OF THE INVENTION

The present invention provides a system for rapid high qualitative and quantitative magnetic separation of rare cells from a fluid sample having a low abundance of the rare cells relative to the rest of the cells, while preserving the vitality the cells.

Rare cells comprise, for example, nucleated red blood cells (NRBC) in Thalassemia patients, or fetal nucleated red blood cells (FNRBC) in the maternal circulation, cancer cells in peripheral blood, fetal or adult stem cells or cells characterized by CD71, CD8, CD34 or CD133 within the circulation.

In some embodiments, the separation provides a sufficient concentration and/or quantity of the rare cells to obtain a significant and reliable clinical, genetic, chemical or other analysis of the cells or parts thereof.

For example, fetal nucleated red blood cells in the circulation of a pregnant woman are very scarce relative to other cells, in the order of 100 ppb or less, preventing reliable genetic analysis of the fetal cells or DNA. According to the methods disclosed herein it is possible to obtain from a routine maternal blood sample an adequate or sufficient quantity of the FNRBC, such as above 95% of the FNRBC present in the sample. Thus the present methods enable efficient separation and the cells obtained may subsequently be used for genetic analysis or diagnosis according to any of the available methods known in the art.

In typical embodiments, the cells of a primary sample (e.g. blood sample) comprising target cells are processed to bind or couple the cells to magnetic beads having coupling or binding specificity to the target cells in the primary sample to form, at least substantially, a sample of magnetized cells among other non-magnetized cells. In some embodiments, the target cells that are bound to the magnetic beads are rare or scarce cell types within a majority of irrelevant non-magnetic cells. In some embodiments, such as when live cells are to be separated (or depleted), the cells are processed such that their viability is preserved and the cells are separated in an environment that maintains (sustains) the cells' viability. Examples of suitable media or carrier fluids are described hereinbelow.

The sample is mixed with a carrier fluid, constituted to sustain living cells, and is then driven through a tube that passes the mixture at a controlled flow rate in the tube irrespective of gravity. The tube passes through one or more magnetization zones (herein also 'separation zones') having a magnetic flux generated and actively controlled by electromagnets. The electromagnets are structured to provide magnetic fluxes formed to attain an effective magnetic separation of rare magnetic target cells. According to preferred embodiments the cells are separated and recovered while the mixture flows at a sufficiently high rate to prevent detrimental effects on the viability of the cells, due to prolonged exposure to suboptimal conditions to sustain cell viability such as lack of aeration.

According to some embodiments the magnetic target cells are retained or separated with an efficiency of at least 50%, alternatively at least 60%, alternatively at least 70%, alternatively at least 80%, alternatively at least 90% or higher of the rare cells originally present in the sample. In other embodiments, the magnetic target cells comprise a majority of the separated cells collected. In various embodiments the magnetic target cells achieve a proportion above 60%, alternatively above 70%, alternatively above 80%, alternatively above 90%, alternatively above 95%, such as 98%, of the separated cells recovered. Each possibility is a separate embodiment of the invention.

The separated magnetic target cells gather at and/or adhere to the tube wall in one or more of the magnetic separation zones. They are then washed (rinsed) by the carrier fluid (or other fluid) into a collecting vessel after the magnetic field is stopped to diminish the attraction of the magnetic cells to the tube.

The present invention also provides mechanisms to assist in efficiently removing and releasing the separated cells from the tube wall, increasing the quantitative yield (recovery) of the separation (in quantity of cells). In some embodiments, the efficiency of washing of the separated magnetic target cells from the tube wall is increased by degaussing the separation zones, removing residual magnetism and decreasing the magnetic attraction of the separated target cells on the tube wall. In other embodiments, the washing is mechanically assisted by at least one of passing one or more air bubbles through the tube, abruptly changing the flow rate inducing shocks in the fluid or vibrating the tube or applying ultrasonic waves to the tube at or in the vicinity of the separation zones.

The electromagnets are designed to provide and concentrate the magnetic flux about the tube with sufficient power for effective separation while avoiding undue or excessive power consumption that might have detrimental effect on the cells or the apparatus e.g., due to heat dissipation Furthermore, in order to achieve rapid yet high quality separation, the system is configured to facilitate flowing of the mixture through a tube having a sufficiently large internal diameter or cross-section at a sufficiently high rate providing rapid separation while avoiding impairing the cells.

In some embodiments, a typical separation cycle of rare cells to purity above 90% and recovery of about or above 90% is completed within several minutes, such as between about 5 and about 15 minutes.

In some embodiments, the system is structured such that the tube passes through, or is disposed at, the separation zones substantially horizontally thereby providing a handy apparatus for placing and operating at various locations including but not limited to sterile compartments or fume hoods. The horizontal configuration is preferred for such confined spaces as opposed to a vertically oriented system.

The separation, retrieval and washing sequence between separation zones, the flow rate, the magnetic field at separation zones, the chemical and physicochemical characteristics of the carrier fluid (e.g. viscosity) and washing fluid, the washing rate, and/or other parameters and operations are all controlled variables. The variables are adapted to provide desired or sufficient results while sustaining the viability of the cells and substantially avoiding aggregation of non-target cells with the magnetic target cells and/or on the tube wall which can reduce the purity and/or yield of the rare cells separation. In some embodiments, the separation working conditions are controlled to yield substantially fractional separation in separation zones according to the magnetic responsiveness of the magnetic target cells. These embodiments are akin to fractional distillation.

It should be noted that while the separation technique outlined above are exemplified herein in efficient separation of rare cells, it is nonetheless efficient in separating and/or depletion of non-rare cells.

It should be noted that the terms 'separation', and conversely 'depletion', do not necessarily imply total separation and conversely total removal of target cells, but practically or sufficiently high qualitative and quantitative separation, and conversely a corresponding depletion.

BRIEF DESCRIPTION OF THE DRAWINGS

Some non-limiting exemplary embodiments of the invention are illustrated in the following drawings.

Identical or duplicate or equivalent or similar structures, elements, or parts that appear in one or more drawings are generally labeled with the same reference numeral, optionally with an additional letter or letters to distinguish between similar objects or variants of objects, and may not be repeatedly labeled and/or described.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

It should be noted that some figures were converted to black-and-white rendering, thereby degrading the pictorial quality such as by reducing certain details or texture or fineness.

Figure 1A:
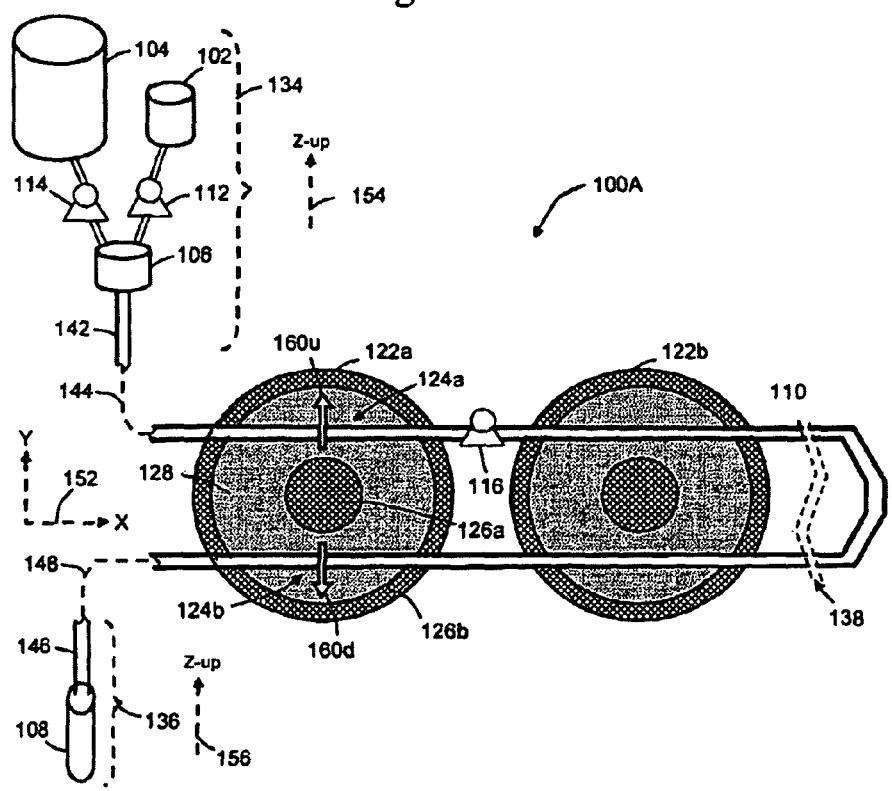
Figure 1B:
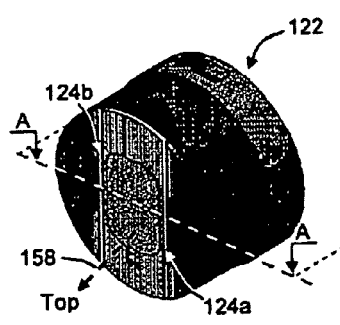
Figure 1C:
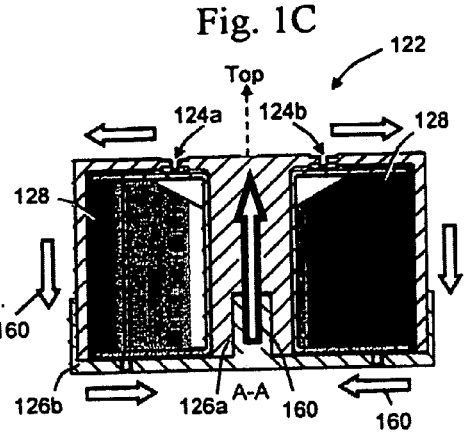
Figure 1D:
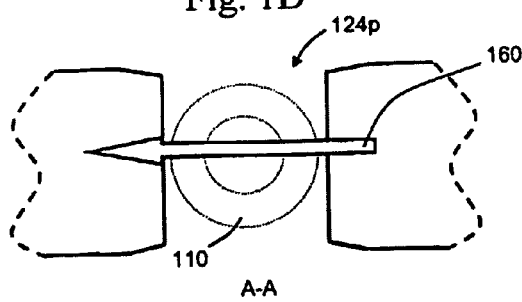
Figure 1E:
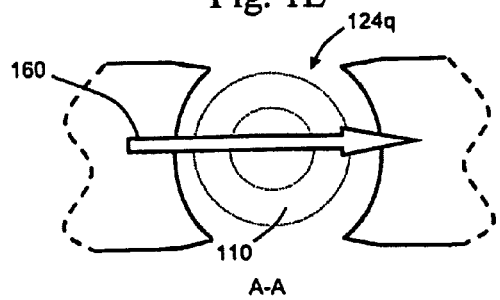
Figure 1F:
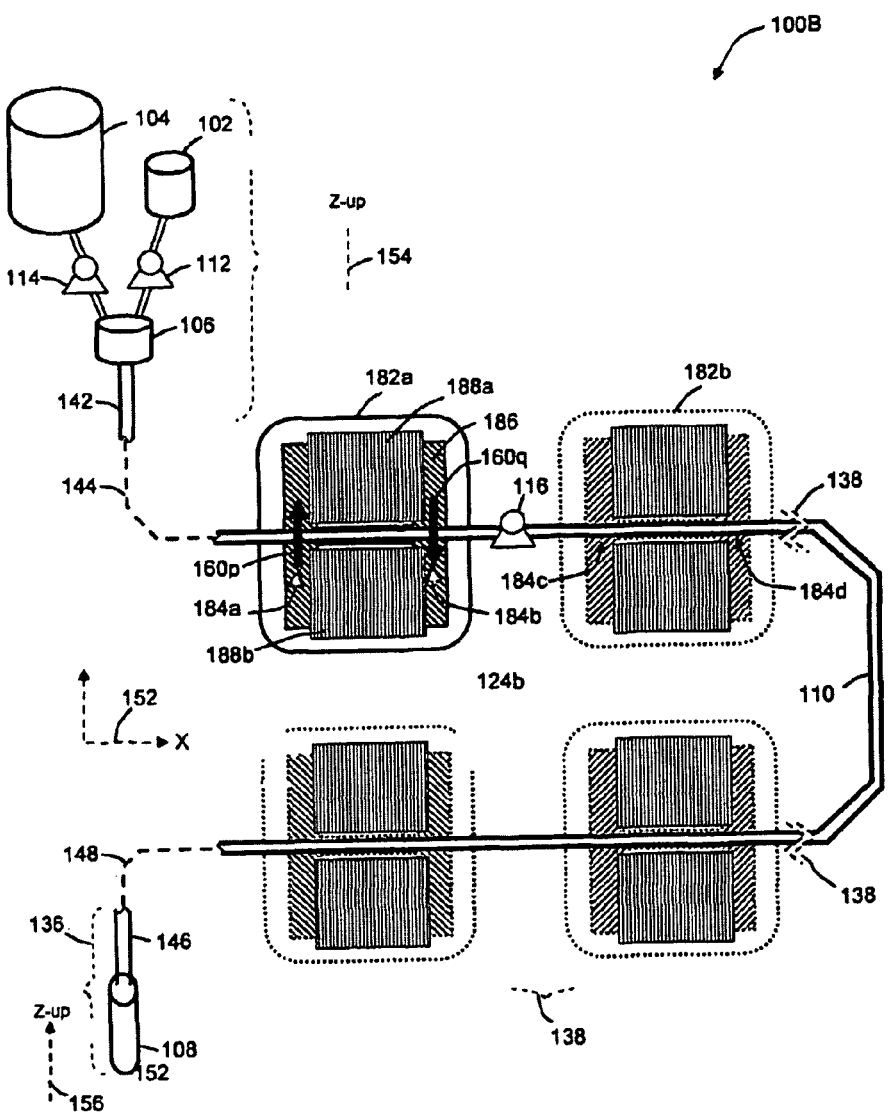
Figure 2A:
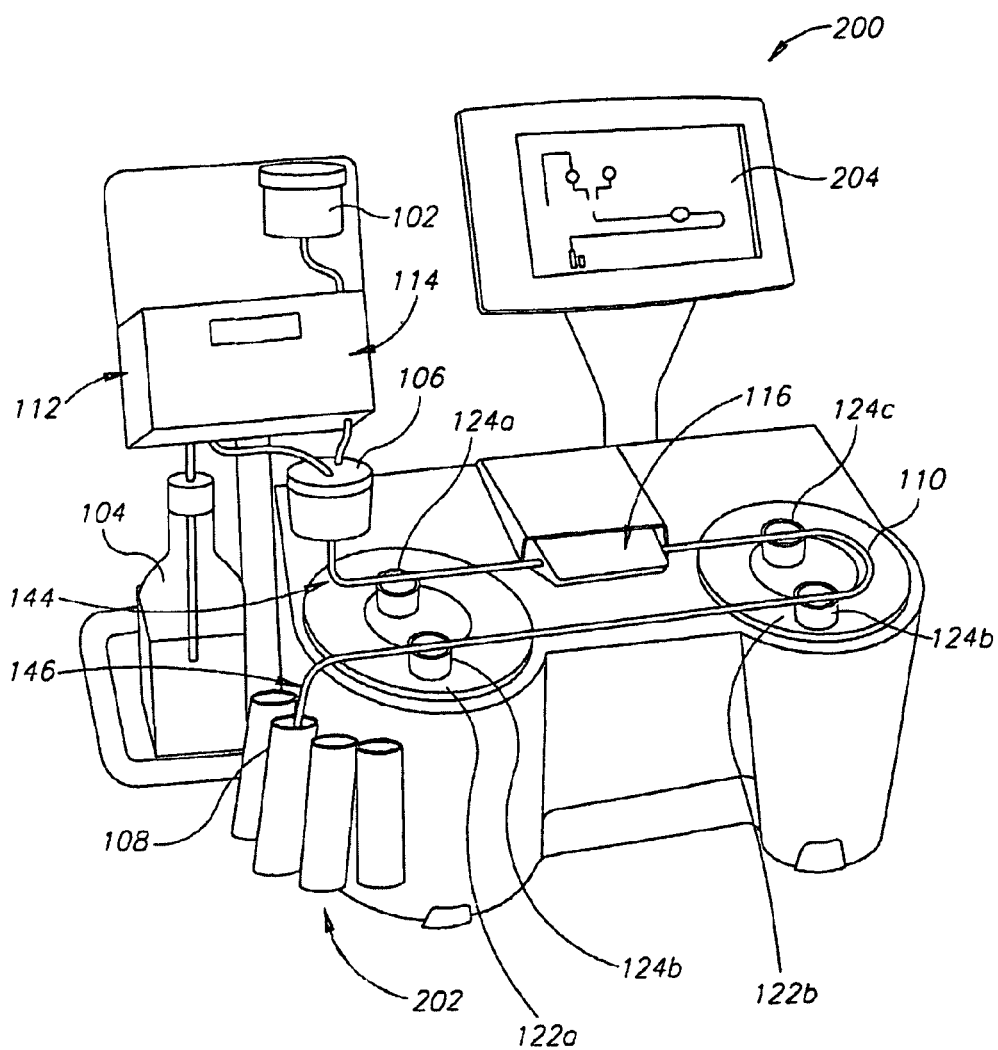

FIG. 1A schematically illustrates a system for separation of rare cells, according to exemplary embodiments of the invention;

FIG. 1B schematically illustrates a perspective view of a separation unit of a system such as of FIG. 1A, according to exemplary embodiments of the invention;

FIG. 1C schematically illustrates a cross-section view of a separation unit of a system such as of FIG. 1A, according to exemplary embodiments of the invention;

FIG. 1D schematically illustrates an enlarged cross-section view of a magnetization zone of a system such as of FIG. 1A, according to exemplary embodiments of the invention;

FIG. 1E schematically illustrates another enlarged cross-section view of a magnetization zone of a system such as of FIG. 1A, according to exemplary embodiments of the invention;

FIG. 1F schematically illustrates another system for separation of rare cells, according to exemplary embodiments of the invention; and FIG. 2A schematically illustrates an external depiction of separation system such as of FIG. 1A, according to exemplary embodiments of the invention.

Figure 2B:
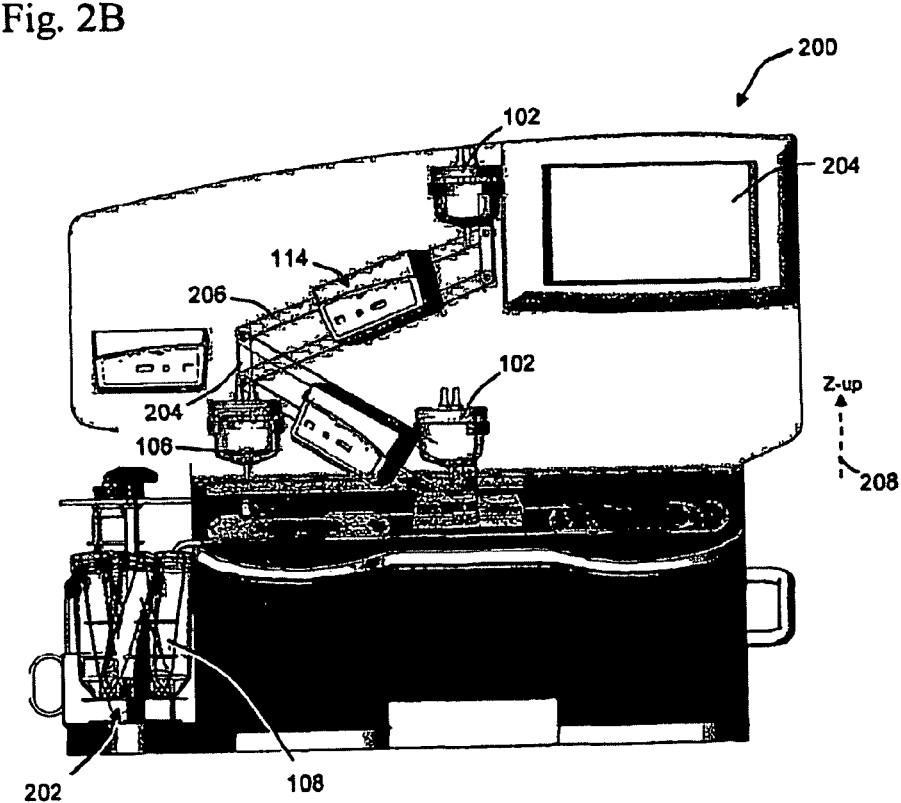

FIG. 2B schematically illustrates an external depiction of separation system such as of FIG. 1A with a mechanism for convenient handling of the sample, according to exemplary embodiments of the invention.

DESCRIPTION OF EMBODIMENTS OF THE INVENTION

The following description relates to one or more non-limiting examples of embodiments of the invention. The invention is not limited by the described embodiments or drawings, and may be practiced in various manners or configurations or variations. The terminology used herein should not be understood as limiting unless otherwise specified.

The non-limiting section headings used herein are intended for convenience only and should not be construed as limiting the scope of the invention.

General Terminology

The terms 'about', 'close', 'approximate' and 'practically' denote a respective relation or measure or amount or quantity or degree that has no adverse consequence or effect relative to the referenced term or embodiment or operation or the scope of the invention.

The terms 'vertical', 'horizontal', 'parallel', 'opposite', 'straight' and other angular and geometrical relationships denote also approximate yet functional and/or practical, respective relationships.

The terms 'preferred', 'preferably', 'typical', 'typically' or 'optionally' do not limit the scope of the invention or embodiments thereof.

The terms 'substantial', 'appreciable' (or synonyms thereof) denote with respect to the context a measure or extent or amount or degree which encompass a large part or most of a referenced entity, or an extent at least moderately or much greater or larger or more effective or more important relative to a referenced entity or with respect the referenced subject matter.

The terms 'negligible', and 'slight' (or synonyms thereof) denote, a sufficiently small respective relation or measure or amount or quantity or degree to have practical consequences relative to the referenced term and on the scope of the invention.

The term 'may' denotes an option or an effect which is either or not included and/or used and/or implemented and/or occurs, yet the option constitutes at least a part of some embodiments of the invention or consequence thereof, without limiting the scope of the invention.

The terms 'comprises', 'comprising', 'includes', 'including', 'having' and their inflections and conjugates denote 'including but not limited to'.

When a range of values is recited, it is merely for convenience or brevity and includes all the possible sub-ranges as well as individual numerical values within and about the boundary of that range. Any numeric value, unless otherwise specified, includes also practical close values and integral values do not exclude fractional values. A sub-range values and practical close values should be considered as specifically disclosed values.

Unless the context indicates otherwise, referring to an object in the singular form (e.g. 'a thing" or "the thing") does not preclude the plural form (e.g. "the things").

Contextual Terminology

In the specification and claims the following terms and derivatives and inflections thereof imply the respective non-limiting characterizations below, unless otherwise specified or evident from the context.

Magnetized/magnetic (cells)—coupled with a ferromagnetic material, such as with magnetic beads.

Target cells—cells typically intended for separation or concentration from other cells (such as for examination or diagnosis), of particular type or having distinct characteristics relative to other cells, such as selective mutual affinity to couple with certain antibodies or other compounds or other particles. In particular embodiments a distinct characteristic is selective affinity to couple or bind with magnetic beads to form magnetic target cells.

Separation—isolation or collection accumulation of target cells from a surrounding fluid bulk, where the bulk is, for example, a fluidic mixture or suspension of emulsion of cells or a combination thereof, implying also concentration or enrichment of target cells relative to the surrounding bulk or a provided sample of cells (obtaining a precipitate in analogy to precipitation or centrifugation).

Depletion—with respect to separation, removal of target cells from the bulk (obtaining a supernatant in analogy to precipitation or centrifugation).

High qualitative (separation, depletion)—high purity, separation of target cells substantially exclusive of other cells, or comprising negligible amount of other cells such as between about 5% and about 1% or less of the separated cells, and conversely a depletion.

High quantitative (separation, depletion)—high recovery, separation of substantially all the target cells, or very high amount of the target cells from the sample, such as between about 95% to about 99% or more or the separated cells, and conversely a depletion.

Magnetic beads—paramagnetic sub-micron particles, such as microbeads or microsphere having diameter or cross-section in the nanometer range (e.g. 20-100 nm), and adapted for selective affinity for coupling or binding with target cells.

Rare cells—cells of particular characteristics which are scarce ("low-abundance") in a source as an organism or other environment, such as about or less than 10 cells/ml (e.g. about 1 cells/ml) or less than 1 ppm (e.g. 1 ppb) relative to other cells in the respective source or environment. For example, fetal nucleated red blood cells (herein also NRBC, FNRBC) or stem cells.

Magnetized/magnetic (cells)—coupled with a ferromagnetic material, such as with magnetic beads.

Cells—biological cells comprising also combination of biological and other particles or compounds optionally of non-biological origin such as magnetic beads, and including for example, blood cells, microorganisms and parts thereof, or other particles of biological origin such as spores or pollen, yet not precluding particles of non-biological origin.

Primary sample (of cells)—a volume comprising cells taken from a cells' source (e.g. blood sample, polluted water or air sample), possibly or optionally physically or chemically or biologically concentrated such as by centrifuge or reagent or antibody.

Sample (of cells)—a volume comprising cells taken from a cells' source (e.g. blood sample, polluted water or air sample), possibly or optionally chemically and/or biologically and/or physically processed and/or altered (e.g. cooled, centrifuged, diluted, coupled with magnetic beads).

Considerable (part or portion)—significant relative amount or quantity such as between about 25% and 80% or more of the referred entity.

'ppm', 'ppb'—parts-per-million ($10^{-6}$), parts-per-billion ($10^{-9}$), respectively.

It should be noted that whenever a reference is made herein to cells attaching or sticking or adhering to a wall of a tube, or similar terms to that effect, it does not necessarily mean that the cells attach directly to the wall, but rather, that they also connect or link or are attracted indirectly to the wall such as by chains of cells or groups of cells.

Overview

A general non-limiting overview of practicing the invention is presented below. The overview outlines exemplary practice of embodiments of the invention, providing a constructive basis for variant and/or alternative and/or divergent embodiments, some of which are subsequently described.

FIG. 1A schematically illustrates a system 100A for separation of rare cells from other cells, according to exemplary embodiments of the invention. Generally, system 100A comprises magnetization zones 124 formed in separation units 122 through which a fluid comprising a sample mixture of magnetic rare cells and other non-magnetic cells passes (flows) in a tube 110 from a sample mixture source 106 and drains to a collection vessel 108. In the following discussions, unless otherwise specified or clearly evident from the context, the term 'target cells' implies 'magnetic target cells'.

A sample container 102 contains sample cells comprising magnetic target rare cells in a life maintaining fluid, and a carrier container (or reservoir) 104 contains a carrier fluid (hereinafter also 'carrier') for carrying the sample in separation system 100A. In some embodiments, typically when live cells are separated, the carrier is a life preserving fluid such as physiological saline, optionally comprising additives such as anti-coagulation ingredients.

The sample and carrier are independently fed by pumps 112 and 114, respectively, into an intermediate container 106 where they are mixed (referred to also as 'mixture container'). Having independently controlled pumps allows adjusting the ratio of the sample to the carrier to facilitate sufficient or desired separation of the target cells, typically with relation to other parameters of system 100A (e.g. number of magnetization zones and field strength). The fluidic mixture of the sample and carrier (hereinafter 'mixture') is fed from mixture container 106 through tube section 142 further on into tube 110 via a connection schematically illustrated as 144.

Typically, the elements indicated by bracket 134 are generally vertical as indicated by arrow 154.

For further reference, FIG. 1B schematically illustrates a perspective view of a separation unit 122 of system 10A (shown with indicated cross-section plane A-A and top surface indicated by arrow 158), and FIG. 1C schematically illustrates a cross-section A-A view of separation unit 122, according to exemplary embodiments of the invention, where FIGS. 1D-E schematically illustrate cross-sections A-A of two exemplary variants of magnetization zones 124.

The mixture form mixture container 106 is supplied into generally horizontally oriented tube 110 disposed on the generally horizontal top surface of one or more separation units 122, as indicated by planar coordinates 152. Separation unit 122 comprises an electromagnet having internal and external cores 126a and 126b, respectively, and a coil 128 winded on internal core 126a, providing magnetization zones 124a and 124b where the field direction is schematically indicated by arrows 160u and 160d, as also shown in FIG. 1C by respective field directions 160.

The mixture fed into tube 110 from mixture container 106 is driven (impelled) in tube 110 by pump 116 that regulates the flow rate independently of gravity and independently of the flow from sample container 102 and carrier container 104 into mixture container 106. As the mixture pass in magnetization zones 124, the magnetic field generated by the electromagnet is formed to attract the magnetized target cells toward the walls of tube 110 and separate and concentrate the target cells from the rest of the mixture onto the walls, while impeding the non-target cells from attaching on the walls.

As the mixture flow through tube 110 and target cells stick to the walls of tube 110, the depleted mixture (substantially without the rare target cells) drains out into a collecting vessel 108 via tube section 146 that connects to tube 110 via a connection schematically illustrated as 148. Typically, elements indicated by bracket 136 are generally vertically oriented as indicated by arrow 156.

Once the separation is finished and the depleted mixture has drained to vessel 108, the electromagnets field generation is stopped, thereby diminishing the attraction of the magnetized target cells to the tube, and the target cells are washed (rinsed) out into another collecting vessel such as another vessel 108. In some embodiments, stopping the magnetic field comprises also degaussing the electromagnets to remove residual magnetism that might still pull and stick the separated target cells to the walls of tube 110, for example by applying temporally decaying alternating currents in the electromagnets, thereby assisting in releasing the separated cells off the tube wall.

In order to enhance the yield of the separated target cells (quantitatively increase of the separation or recovery), in some embodiments in addition or alternatively to degaussing one or more measures are taken to promote releasing the target cells from the wall of tube 110. For example, flowing one or more air bubbles that push on the target cells, and/or vibrating the tube such as by one or more piezoelectric elements and/or applying ultrasound on the tube, at least about magnetization zones 124, or abruptly changing the flow rate thereby inducing shocks in the fluid. Concurrent with and/or subsequent to applying the dislodging promoting means the target cells washed out by the carrier, or by another fluid such as from another container, and the constituency (e.g. viscosity) and/or flow rate of the washing fluid are optionally set or adjusted to in order to wash out substantially all the separated target cells.

It should be noted that in various embodiments any number of separation units 122 may be used in embodiments of system 100A, including a single unit, as shown by breaking/continuation indications 138.

Separation System Variants

FIG. 1F schematically illustrates another system 100B for separation of rare cells, according to exemplary embodiments of the invention.

System 100B is similar to system 100A, apart that instead of separation units 122 of system 100A separation units 182 of different design are used in system 100B.

Separation unit 182 comprises an electromagnet comprising a core 186 around which coils such as 188a and 188b are winded generating magnetic field indicated by arrows 160p and 160q about magnetization zone 184 such as 184a and 184b, respectively. Any number of separation units 182 may be used in embodiments of system 100B, including a single unit, as shown by breaking/continuation indications 138.

FIGS. 2A-B schematically illustrate an external depiction 200 of separation system such as 100A, according to exemplary embodiments of the invention. The indicated parts are as or similar to those of system 100A as described with respect to FIGS. 1A-C. System 200 is typically controlled by one or more processors or computers operated according to one or more programs stored on a computer-readable medium and handled, for example, via a touch panel 204 and/or via a mouse and/or keyboard and/or any other human interface device such a dedicated keypad or a remote control unit.

In some embodiments, collecting vessels such as 108 are mounted on a mechanism, such as carousel (indicated as 202), that shifts or rotates the appropriate vessel to a position for draining tube 110 according to the system operation procedures. For example, during separation a vessel for collecting the depleted mixture is placed for the drain, and during collection of the target cells another vessel is place at the drain.

As a separation system such as system 200 is typically used in controlled environments such as sterile compartments or fume hoods, access to mount or remove sample container 102 or fill the sample or add ingredients to the sample may be in some cases limited or awkward if sample container 102 (or mounting elements thereof) is fixedly disposed in a high position (relative to the rest of the system such as level of magnetization zone 124). In some embodiments, a mechanism to provide convenient access to sample container 102 is implemented.

FIG. 2B further illustrates a mechanism 206 for convenient handling of sample container 102, according to exemplary embodiments of the invention. Mechanism 206 is structured as a parallelogram where one side 204 is fixedly mounted on the framework of system 200 and the other one is moveable between an upper position and a lower position, the latter depicted as an overlay, and upward direction is indicated by arrow 208.

Optionally other mechanisms may be used, including for providing convenient access to other parts of a system such as system 200.

Equipment/Variations

Generally, systems 100A, 100B and 200 (FIGS. 1A, 1F and 2A-B, respectively), share common characteristics as described above, and will be generally referred to in the following descriptions, without limiting, also as system 100 (also 'the system'). FIGS. 1A-F and 2A-B are also referred the following descriptions.

The construction of the electromagnets and magnetization zones 124 and 184 in system 100A and 100B, respectively, and the shape, directions and intensity of the magnetic field (e.g. spatial distribution) generated by the electromagnet, as well as the number of the magnetization zones, each optionally having different field shape and/or intensity, are configured or determined or tuned to achieve an effective separation of the rare target cells on the tube wall. The field flux at the magnetization zones effect a separation of the magnetized cells while impeding the non-target (and not-magnetized) cells from attaching to the tube wall, resulting in a concentration of the rare cells in a range from about 95% to about 99% or more, such as 98%, practically with no non-target cells or negligible amount thereof.

In some embodiments, the non-target cells are impeded by hindering or delaying the movements thereof in the fluid mixture towards the tube wall, optionally by taking into account the properties of the carrier or mixture such as viscosity or elasticity. In some embodiments, the composition of the carrier (or the mixture to that matter) are set or selected or adjusted such as by additives to effect the adequate hindrance properties, while still allowing the movements of the magnetized target cells towards the tube wall under the pull of the magnetic field.

The magnetic flux shape and intensity at the magnetization zones is configured, for example, by one or more of the shape and construction (e.g. structure, materials) of a core (e.g. 126 or 186), the shape and windings of a coil (e.g. 128 or 188), the current intensity in a coil (including optionally temporal variation of the current) and the formation (e.g. groove, fixture) where the tube (e.g. tube 110) is disposed. In some embodiments, in order to achieve the separation as described above, the electromagnets are configured such that at each magnetization zone a considerable amount of the magnetized rare cells in the flowing mixture (e.g. 50% or more) are attracted onto the tube wall yet with negligible amount of or practically no non-target cells. In some embodiments, the electromagnets are designed and constructed according to design rules and/or expertise and modification are determined by checking the effectiveness of separation, for example comparing the concentration or distribution of the rare cells in the sample and in separated collection by methods of the art (e.g. cytometry or MACS). Subsequently the electromagnets or magnetization zone are adjusted or trimmed or tuned to improve the results towards a goal such as separation concentration of 95% and above.

It is noted that the path from mixture container 106 to collecting vessel 108 is essentially a continuous conduit or tube, where tube such as 110 and tube sections such as 142 or 146 and connections 144 and 148 are of the same or of different diameter or cross-section. In some embodiments, the cross-section of tube 110 may vary along the length thereof thereby varying the flow rate, optionally having diameter or cross-section about magnetization zones adapted to promote adherence of the target cells to the tube wall and/or prevent adherence of non-target cells to the wall of tube 110 or the target cells and/or prevent coagulation of the non-target cells which may hinder the mixture flow.

In some embodiments, the inner diameter of tube 110, at least about magnetization zone 124 or 184 is about or larger than 2 m to enable sufficient flow rate to achieve rapid separation.

The connections indicated by 144 and 148 are tube sections such as curved tube or knee-like tube, and are typically bends in tube 110 (see for example, FIGS. 2A-B), and connect the generally vertical tubes section 142 and 146 to the generally horizontal tube 110. Optionally or alternatively, the separation system may be structured such that sections of the tube or conduit from mixture container 106 to collecting vessel 108 may be in other orientations, between a substantially horizontal general orientation (e.g. sample container 102 and mixture container 106 are about the same level) to a substantially vertical general orientation or any other variation.

Typically, the tubes such as 110 or 142 or 146 and connections 144 and 148 are made of or coated with biocompatible material to preserve the live cells, such as silicone tubes. Typically the tubes are flexible and bendable and are elastically compressible (e.g. resilient to compression).

Impelling pump 116 may be disposed at any practical section on the path between mixture container 106 to and collecting vessels 108, such as before the first separation unit such as 122 or 182, or after the last separation unit.

In some embodiments, any number of separation units or magnetization zones or electromagnets may be used, as shown by breaking/continuation indication 138, implying also a smaller number of electromagnets or units or zones, optionally only one element thereof, as well as a shorter tube. Optionally a plurality of pumps such as pump 116, typically synchronized, may be used to flow the mixture in tube 110.

In some embodiments, pumps 112, 114 and 116 are any pumps that maintain the vitality of the cells and/or provide regulated flow, such as peristaltic pumps.

It should be noted that although separation units 122 or 182 comprise two magnetization zones 124 each, yet units 122 or 182 or other units may be designed to have one or more than two magnetization zones, optionally of different construction and generated magnetic field.

In some embodiments, sample container 102 is disposable and has a capacity of about 50 ml and used for only for one separation whereas in some embodiments carrier container 104 is a larger bottle or other container for supplying carrier fluid for numerous separations. In some embodiments, tube 110 (or in fact the continuous tube comprising tube 110 and sections 142 and 146 and connections 144 and 148) is made of disposable and used for one separation only and is made of silicone tubing 1.98*3.18. Typically collection vessels are similar to test-tubes and are disposable.

In some cases where the vitality of the cells is not mandatory or the sample is of non-animate particles the fluids such as carrier or washing fluids are not necessarily life sustaining, and the tubes are not necessarily biocompatible, allowing larger selection of constituents and components for particular properties such as viscosity, elasticity or flow regime.

Magnetization Zones

The electromagnets are designed to provide and concentrate the magnetic flux in the magnetization zones for effective separation with power efficiency by avoiding excessive or superfluous power consumption that might have detrimental effect on the cells or the apparatus. For example, excessive heat dissipation that can damage the cells or coagulate the cells, or change the viscosity of the carrier, or deform the electromagnets. Keeping the power consumption to a substantially minimal or nominal value, while providing adequate flux for separation, enables also to avoid cooling mechanisms thereby providing a simple compact and reliable apparatus.

Furthermore, in order to achieve rapid yet high quality separation the system is configured to facilitate flowing the mixture in a tube having a sufficiently large internal diameter or cross-section, e.g. about 2 mm, at a sufficiently high rate, e.g. about 2 ml/min, providing rapid separation while avoiding impairing the cells which may occur if the rate is inadequately low or the tube is inadequately narrow (e.g. about 1 mm or less) resulting with forces in the flowing fluid, such as shear, that may be detrimental to the cells such as coagulation of cells. Accordingly, the electromagnets are structured and controlled to efficiently separate living rare cells that flow in a high rate and in wide tube as described.

FIG. 1D schematically illustrates an enlarged cross-section view of a magnetization zone 124p such as zone 124 of separation unit such as unit 122, where the disposition of tube 110 is schematically depicted by a section of the tube. Magnetization zone 124p is formed as generally parallel flat surfaces separated by a gap for disposing a section of tube 110 in the magnetic field flux indicated by arrow 160 (the direction of the field may be opposite as shown in magnetization zones 124a and 124b in FIG. 1C). In some embodiments, the gap is about 3 mm or more to allow placing a sufficiently wide tube 110 to facilitate rapid separation.

FIG. 1E schematically illustrates an enlarged cross-section view of a magnetization zone 124q such as zone 124 of separation unit such as unit 122, where the disposition of tube 110 is schematically depicted by a section of the tube. Magnetization zone 124q is formed as generally opposing rounded surfaces for further concentration of the magnetic flux (such as relative to magnetization zone 124p) substantially without additional power. The rounded surfaces are separated by a gap for disposing a section of tube 110 in the magnetic field flux indicated by arrow 160 (the direction of the field may be opposite as shown in magnetization zones 124a and 124b in FIG. 1C). In some embodiments, the gap allows placing a sufficiently wide tube 110, such as of external diameter of about 3 mm, to facilitate rapid separation.

Table-1 below provides as a function of current an example of the efficiency of producing and concentration magnetic field flux at magnetization zones 124, and the better efficiency of the round surfaces of magnetization zone 124q relative to the flat surfaces of magnetization zone 124p. The coil of the electromagnet (e.g. coil 128 of separation unit 124) is made of 2000 windings of a wire of 1.1 mm thick, resulting in a resistance of 9.1Ω.

The described and listed values are close approximations.

TABLE 1

| Flux (mT) | Current (Amp) Flat surfaces | Current (Amp) Round surfaces |
|---|---|---|
| 100 | 0.145 | 0.09 |
| 200 | 0.28 | 0.22 |
| 300 | 0.42 | 0.31 |
| 400 | 0.58 | 0.45 |
| 500 | 0.77 | 0.60 |
| 600 | 1.03 | 0.80 |
| 700 | 1.49 | 1.12 |
| 800 | 2.12 | 1.60 |
| 900 | 3.47 | 2.71 |
| 930 | — | 3.16 |
| 956 | 5.15 | — |

Operation

In order to achieve high quantitative and qualitative separation yield of rare cells, system 100 is operated, optionally at least partially under a programmed processor, according to certain procedures and parameters, some of which are described below.

In the process of coupling target rare cells with the magnetic beads (see also below) some cells typically couple with larger amount of beads than others, resulting with magnetic target cells having different magnetic attraction (force under given magnetic field). Assuming, for clarity and simplicity, that only one magnetization zone (e.g. magnetization zone 124) is used, than applying a strong magnetic field sufficient to attract substantially all the target cells may, in some cases, pull the cells such that they form chunks or lumps that adhere to the wall of the tube (e.g. tube 110, hereinafter 'the tube') resulting in low qualitative separation yield. Moreover, possibly and probably, as the target cells drift towards the tube wall they would pull with them non-target cells that may adhere or be concealed in the lumps of cells or coagulate on or with the target cells, resulting in lower qualitative separation. On the other hand, if a weak magnetic field is applied than only the target cells with strong attraction (coupled with relatively large amount of beads) are separated, the rest flowing out with the partially depleted mixture resulting in low quantitative separation.

Therefore, in some embodiments, different intensities of magnetic field and/or different spatial distributions of the magnetic flux are applied on different magnetization zones. The fields are then adjusted such that the target cells are separated and stick to the tube wall sufficiently to withstand the flow of the mixture, negligibly or without attracting non-target cells, while substantially or entirely (at least practically) washed out and released when the magnetic field is terminated. For example, the first magnetization zone provides moderately strong field, attracting the target rare cells with small amount of magnetic beads so that non-target cells are practically not pulled and not carried to the tube wall or coagulate with the target cells. At a subsequent magnetization zone a lower field is applied attracting the target cells with larger attraction y et practically without pulling non-target cells. Such a scheme with several magnetization zones are may be used, each with different magnetic field intensity and flux distribution.

In some embodiments, in order to reduce space and costs, the tube may pass through given number of magnetization zones, possibly in one or more loops, and the field intensities adjusted to fractionally separate the rare target cells without, or practically without, pulling and capturing non-target cells. Optionally or alternatively, in some embodiments with a given number of magnetization zones (possibly even one), a moderately weak field is used for target cells with high attraction, and subsequently the field is increased and the mixture is recycled back to separate the target cells with higher attraction. Optionally or alternatively, with a given number of magnetization zones a fraction of the rare target cells are separated with certain field intensity, the field terminated and the separated target cells are washed out and collected, and the cycle is repeated again with different field intensities, thus sequentially separating portions of the rare target cells.

In some embodiments, the magnetic flux is formed with varying intensities (gradients) to attract a variety of magnetized rare cells with only a negligible, if any, non-target cells or accumulation thereof. Similarly, in some embodiments, the magnetic flux is temporally variable (with a rate respective to the mixture flow) to attract a variety of magnetized rare cells with only a negligible, if any, non-target cells or coagulation thereof. In some embodiments, a combination of spatially varying and temporally varying flux is tuned to achieve high qualitative and quantitative rare cells separation.

The number of magnetization zones and/or the number of separation cycles may be adjusted allowing tuning the system to a fine differential or fractional separation of rare target cells with a cumulative outstanding qualitative and quantitative separation yield.

It is noted that in the foregoing description qualifying Willis such as strong, weak moderately, large, low or high merely imply relative amounts or intensities to illustrate different cases.

Optionally or additionally, in some embodiments, other parameters are adjusted, possibly and optionally with respect to parameters such as magnetic field intensity or spatial distribution or type of cells and/or other parameters such as temperature. For example, the flow rate and/or viscosity and/or elasticity of the mixture or carrier fluid may be adjusted such as to allow separation of target cells yet preventing, at least substantially, coagulation of non-target cells. In some embodiments, the carrier fluid is used to wash out the separated target cells, yet in some embodiments the washing fluid is different from the carrier fluid. The flow regime and rate of the washing fluid is optionally adjusted to promote dislodging (e.g. promote the removal or release) the target cells from the tube wall, such abruptly altering the flow thereby inducing turbulences or shocks that help eroding or destabilize the target cells on the tube wall.

In some embodiments, a typical cycle for high qualitative and quantitative separation yield of rare cells is completed within several minutes, such as about 15 minutes at a throughput of about 2 ml/min where further tuning of the operation parameters and/or additional equipment (e.g. more separation units or magnetization zone for practically simultaneous fractional separation or simultaneously using a plurality of tubes) may reduce the separation cycle time. In some embodiments, the order of magnitude of the magnetic field flux density generated by the electromagnets in a magnetization zone is of 1 T (Tesla), and in some embodiments, a considerable portion such as more than half (e.g. about 80%) of the target cells are separated in the first one or two magnetization zones (first separation unit such as unit 122).

It is noted that in some embodiments, promoting the release of separated cells off the tube (e.g. degaussing, bubbling, vibrations) is carried out prior to and/or concurrent with washing the cells out of the tube.

It should be noted that when high quality or purity depletion is indented (rather than collection of the target cells) sufficiently strong magnetic fields may be applied such as stronger than used for collection, on the expense of non-target cells adhering to the wall and/or coagulating.

Sample

The sample is typically obtained from a primary sample comprising rare cells intended for examination (target cells) which were processed to specifically couple with magnetic beads. For example, a blood sample from a pregnant woman where rare fetal nucleated red blood cells (FNRBC) as target cells are expected to be present, or stem cells from blood or amniotic fluid.

In some exemplary cases the primary sample source is other physiological fluid such as lymph or urine whereas in some cases the source is non-biological and the cells are bacteria or other biological particles such as pollen or spores collected from sources such as water or air or other environments.

In some embodiments, the target cells are, in fact, not cells but rather other micro-particles (e.g. about or less than 1 μm) of any material or composition where the target particles can selectively couple of bind with magnetic beads.

Outline of an Operational Procedure

According to the descriptions above in some embodiments the system is used to separate with high qualitative and quantitative yield magnetized cells from a fluid mixture of cells, by (a) providing a sample of cells comprising magnetized rare cells, and (b) flowing a mixture of the sample of cells in a carrier fluid inside a tube disposed about a magnetization zone having a magnetic flux, generated by an electromagnet, sufficient to attract a majority of the magnetized rare cells from the mixture onto the tube wall while impeding other cells from attaching to the tube wall, thereby separating magnetized rare cells on the tube wall.

In some embodiments, the magnetized cells are rare cells in low abundance relative to there rest of the cells.

In typical embodiments, once the separation of the magnetized cells rare cells from the mixture is completed (or practically completed), the magnetic flux is terminated (diminishing the attraction of the cells) and the separated magnetized rare cells are washed out of the tube.

In some embodiments, the washing of the separated cells is preceded or accompanied by activation of mechanism to promote dislodging the separated magnetized rare cells off the tube wall, such as degaussing, bubbling or vibrating the tube.

Exemplary Procedure

A primary blood sample of a few ml (e.g. 5 ml) is taken from a pregnant woman.

The sample is prepared and coupled with magnetic beads similar or as defined at the kit protocol in http://tools.invitrogen.com/content/sfs/manuals/11331D-Dynal-CD4-Positive-Isolation-Kit-(rev003).pdf The prepared sample is placed in the disposable sample container (e.g. container 102).

About 3 ml of washing buffer (carrier fluid) of PBS+2 mM EDTA+0.5% BSA are placed in the carrier container (e.g. 104) and the corresponding pump (e.g. pump 114) is switched on flowing the washing fluid (carrier fluid) at about 2 ml/min to fill the tubing (e.g. tube 110 and connecting sections) in order to prepare the device, including filling mixture container (e.g. container 106) for separation and then the pumps are switched off.

The magnetic field at the separation units (units 122) is set at about 450-800 mT and impelling pump (e.g. pump 116) is switched on to flow the mixture at about 1 ml/min. When just a few ml (e.g. 2 ml) remain in the mixture container, the impelling pump is switched off and the system is washed by about 15 ml washing fluid at about 2 ml/min rate.

The magnetic field is switched off and the electromagnets are degaussed.

The target cells are washed to collecting vessel (e.g. vessel 108) by about 3 ml washing fluid at about 2 ml/min rate.

REFERENCES (1) Schmorl G. Pathologisch-anatomische undersuchungen uber puerperal-eklampsie. Leipzig; Vogel, 1893.
(2) Walknowska J, Conte F A, Grumbach M M. Practical and theoretical implications of fetal/maternal lymphocyte transfer. Lancet 1969; 1: 1119-1122.
(3) Bianchi D W, Flint A F, Pizzimenti M F, Knoll J H M, Latt S A. Isolation of fetal DNA from nucleated erythrocytes in maternal blood. Proc Natl Acad Sci 1990; 87:3279-3283.
(4) Wessman M, Ylinen K, Knuutila S. Fetal granulocytes in maternal venous blood detected by in situ hybridization. Prenat Diagn 1992; 12:993-1000.
(5) Bianchi D W, Zickwolf G W, Weil G J, Sylvester S, DeMaria M A. Male fetal progenitor cells persist in maternal blood for as long as 27 years postpartum. Proc Natl Acad Sci 1996; 93:705-708.
(6) Bianchi D W, Williams J M, Sullivan L M, Hanson F W, Klinger K W, Shuber A P. PCR quantitation of fetal cells in maternal blood in normal and aneuploid pregnancies. Am J Hum Genet 1997; 61:822-829.
(7) Lamvu G, Kuller J A. Prenatal diagnosis using fetal cells from the maternal circulation. Obstet Gynecol Survey 1997; 52:433-437.
(8) Bianchi D W, Simpson J L, Jackson L G, et al. 2002. Fetal gender and aneuploidy detection using fetal cells in maternal blood: analysis of NIFTY I data. National Institute of Child Health and Development Fetal Cell Isolation Study. Prenat Diagn 22: 609-615.
(9) Chui R W, et al. 2008. Noninvasive prenatal diagnosis of fetal chromosomal aneuploidy by massively parallel genomic sequencing of DNA in maternal plasma. PNAS 105(51):20458-63.

The invention claimed is:

1. A method comprising:
   (a) providing a magnetic separation system that comprises:
      a sample container,
      a first pump disposed downstream from said sample container,
      a carrier container,
      a second pump disposed downstream from said carrier container,
      a mixture container disposed downstream from said first and second pumps,
      a plurality of electromagnets,
      a tube extending from said mixture container, passing about said plurality of electromagnets, and terminating at a plurality of collection vessels,
      a third pump associated with said tube;
   (b) operating said first and second pumps to separately feed, into said mixture container, a sample fluid from said sample container and a carrier fluid from said carrier container, wherein the sample fluid comprises magnetized cells and non-magnetized cells,
   (c) operating said plurality of electromagnets to generate magnetic flux, and at the same time operate said third pump to cause a mixture of the sample fluid and the carrier fluid to flow inside said tube about said plurality of electromagnets, such that:
      a majority of the magnetized cells are attracted to a wall of said tube, about said plurality of electromagnets, and
      a majority of the non-magnetized cells are drained to a first collection vessel of said plurality of collection vessels,
   (d) operating said plurality of electromagnets to terminate the magnetic flux, and at the same time operating said second and third pumps to feed a washing fluid from said carrier container, through said mixture container and into said tube, such that attracted magnetized cells are dislodged from the wall of said tube and are washed, with the washing fluid, to a second collection vessel of said plurality of collections vessels.

2. The method according to claim 1, wherein the tube is disposed generally horizontally about the plurality of electromagnets.

3. The method according to claim 1, wherein the plurality of electromagnets is arranged about a generally horizontal plane for disposing the tube generally horizontally about the plurality of electromagnets.

4. The method according to claim 1, wherein the tube is disposed generally vertically about the plurality of electromagnets.

5. The method according to claim 1, wherein the plurality of electromagnets is arranged about a generally vertical plane for disposing the tube generally horizontally about the plurality of electromagnets.

6. The method according to claim 1, wherein the tube is disposed about the plurality of electromagnets in a successful manner, such that each successive electromagnet of the plurality of electromagnets attracts onto the wall of the tube a majority of the magnetized cells remaining in the flowing mixture following attraction by a preceding electromagnet of the plurality of electromagnets.

7. The method according to claim 1, further comprising operating at least one mechanism to promote the dislodging of attracted magnetized cells from the wall of said tube.

8. The method according to claim 7, further comprising operating said at least one mechanism to degauss the plurality of electromagnets.

9. The method according to claim 7, wherein:
- the mechanism comprises an apparatus configured to flow an air bubble in the washing fluid inside the tube; and
- the method further comprises operating said apparatus and said third pump to cause the air bubble to flow in the washing fluid inside the tube.

10. The method according to claim 7, wherein:
- the mechanism comprises an apparatus configured to vibrate the tube; and
- the method further comprises operating said apparatus to vibrate the tube.

\* \* \* \* \*